(12) United States Patent
Takada et al.

(10) Patent No.: US 6,344,437 B1
(45) Date of Patent: *Feb. 5, 2002

(54) MEDICINE DRINK FOOD AND FEED HAVING AN ACTION OF STRENGTHENING BONE

(75) Inventors: Yukihiro Takada, Kawagoe; Seiichiro Aoe, Sayama; Ken Kato, Ohmiya; Yasuhiro Toba; Junichi Yamamura, both of Kawagoe, all of (JP)

(73) Assignee: Snow Brand Milk Products Co., Ltd., Hokkaido (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/819,110

(22) Filed: Mar. 17, 1997

(30) Foreign Application Priority Data

Mar. 28, 1996 (JP) .............................. 8-099059

(51) Int. Cl.⁷ ...................... A61K 31/593; A61K 38/39; C07K 14/78
(52) U.S. Cl. ............................. 514/2; 514/12; 514/167; 514/801; 530/354; 530/355; 530/356; 552/653
(58) Field of Search ................................ 530/356, 354, 530/355; 514/2, 12, 167, 801; 552/653

(56) References Cited

U.S. PATENT DOCUMENTS

| | | | |
|---|---|---|---|
| 4,294,753 A | * 10/1981 | Urist | 260/112 |
| 4,698,326 A | * 10/1987 | Sauk et al. | 514/7 |
| 4,804,745 A | 2/1989 | Koepff et al. | 530/356 |
| 5,043,170 A | * 8/1991 | Borenstein et al. | 426/73 |
| 5,162,506 A | 11/1992 | Hadden | 530/412 |
| 5,208,219 A | * 5/1993 | Ogawa et al. | 514/12 |
| 5,522,888 A | * 6/1996 | Civerchia | 623/4 |
| 5,948,766 A | * 9/1999 | Milan et al. | 514/21 |

FOREIGN PATENT DOCUMENTS

| | | |
|---|---|---|
| CH | 494 250 A | 9/1970 |
| EP | 0 254 289 A | 1/1988 |
| EP | CN 1 077 630 A | 10/1993 |
| EP | CN 1077630 | * 10/1993 |
| WO | WO 96 05851 | 2/1996 |
| WO | WO9605851 | * 2/1996 |

OTHER PUBLICATIONS

Krishnakumar et al. (1995), "Gelatin Global Supply and Demand," *International Food Ingredients* pp. 17–19.

EP 97 10 5286 European Search Report (Dec. 8, 1998).

J.I. Boye et al., "Factors Affecting Molecular Characteristics of Whey Protein Gelation" *Int. Dairy J.* 5:337–353 (1995).

M. Britten et al., "Emulsifying Properties of Heat–Denatured/Undenatured Whey Protein Composite Blends" *IDF Special Issue 9303*, IDF Seminar, Munich, Germany, Aug. 25–28, 1992, pp 368–374.

B.C. Ghosh et al., "Rennetability of Milk Containing Different Heat–Denatured Whey Protein" *Milk Science International* 51(1):28–31 (1996).

A.J.R. Law et al., "Heat–Induced Changes in the Whey Proteins and Caseins" *Milk Science International* 49(3):125–1129 (1994).

D.J. McClements et al., "Physical Properties of Cold–Setting Gels Formed from Heat–Denatured Whey Protein Isolate" *J. Sci. Food Agric.* 69:7–14 (1995).

J. Merenmies et al., "30–kDa Heparin–Binding Protein of Brain (Amphoterin) Involved in Neurite Outgrowth" *J. Biol. Chemistry* 266(25):16722–16729 (1991).

B. Pentecost et al., "Isolation and Partial Sequence of Bovine cDNA Clones for the High–Mobility–Group Protein (HMG–1)" *Bioscience Reports* 4:49–57 (1984).

K. Sato et al., "Preparation of a Gel of Partially Heat–Denatured Whey Protein by Proteolytic Digestion" *Milk Science International* 50(7):389–392 (1995).

A.R. Shakoori et al., "Differential Expression of the Chromosomal High Mobility Group Proteins 14 and 17 During the Onset of Differentiation in Mammalian Osteoblasts and Promyelocyte Leukemia Cells" *J. Cellular Biochemistry* 51:479–487 (1993).

* cited by examiner

*Primary Examiner*—Christopher S. F. Low
*Assistant Examiner*—Anish Gupta
(74) *Attorney, Agent, or Firm*—Testa, Hurwitz & Thibeault, LLP

(57) ABSTRACT

The present invention is to provide a novel medicine, drink, food or feed having an action of strengthening bone. More specifically, the present invention is to provide a medicine, drink, food or feed combined with collagen, fraction containing collagen or degradation product thereof. Fraction containing collagen was prepared by mincing skin corium layer into pieces, defatting it and lyophylization or by pulverizing bone, decalcifying it and lyophylization. Oral administration of these can stimulate proliferation of osteoblast, inhibit bone resorption and strengthen bone. They can be useful for improvement of osteoporosis, bone fracture, bone pain, etc.

7 Claims, 1 Drawing Sheet

MEDICINE DRINK FOOD AND FEED HAVING AN ACTION OF STRENGTHENING BONE

FIELD OF THE INVENTION

The present invention relates to a medicine, drink, food and feed which is having an action of strengthening bone. The medicine, drink, food or feed combined with collagen, fraction containing collagen, and/or degradation product that has effects of promoting bone formation, strengthening bone, preventing and treating bone metabolic diseases such as osteoporosis, bone fracture, bone pain and so on.

BACKGROUND OF THE INVENTION

Accompanying the prolongation of the human life span, the incidence of metabolic bone diseases such as osteoporosis, bone fracture, bone pain etc., has recently increased. In bone tissue, bone formation and bone resorption are always occurring. While the balance of bone formation and bone resorption is kept in one's youth, bone resorption exceeds bone formation due to various causes as one's age increases (uncoupling). And when bone resorption persists for a long duration, bone tissue becomes fragile, which causes metabolic bone diseases such as osteoporosis, bone fracture, bone pain, etc.

As conventional methods of preventing or treating metabolic bone diseases by inhibiting uncoupling include (1) calcium supplemented diets, (2) light exercise, (3) sunbathing, (4) medicinal therapy, etc. As for calcium supplemented diets, calcium salts such as calcium carbonate, calcium phosphate, etc., and naturally occurring calcium-containing preparation, such as bovine bone powder, egg shell, fish bone powder, etc. are used. They are, however, not necessarily good enough for oral intake. As light exercises, jogging or walking may be recommended. However, they are troublesome to a person who becomes weak and quite difficult to an immobilized aged person. Sunbathing is believed to be good for supplementing the active form of vitamin $D_3$ but is not sufficient. As medicinal therapy, 1 $\alpha$-hydroxyvitamin $D_3$ and/or calcitonin may be used and they are known to be effective for treating osteoporosis. However, these medicines can not be used as food sources.

On the other hand, collagen is known as a main protein component of animal connective tissue and occupies nearly 30% of total protein in mammalian, especially, human whole body. This collagen is a protein of cellular matrix and can be defined to be a substance having an $\alpha$-chain which is a helical portion consisting of 3 polypeptide chains and forming a multi-molecular complex. Further, collagen forms intercellular matrix with glyco-proteins, such as proteoglycan, fibronectin, laminin etc., and is an essential component for exhibiting its function as assembled tissue of cells in multi-cellular biological organism.

The present inventors have investigated to find a substance capable of strengthening bone which is useful for food sources. Eventually, we found out that a fraction containing collagen such as skin protein fraction or bone protein fraction has an effect of promoting proliferation of osteoblast. Further, the present inventors found that degradation products of an the fraction containing collagen also have an effect of promoting proliferation of an osteoblast and accomplished the present invention.

SUMMARY OF THE INVENTION

Accordingly, an object of the present invention is to provide a medicine, drink, food or feed having an action of strengthening bone. More specifically, the present invention is to provide a medicine, drink, food and feed having an action of strengthening bone combined with collagen, fraction containing collagen and/or degradation product thereof.

Another object of the present invention is to provide a medicine, drink, food or feed combined with collagen, fraction containing collagen or degradation product thereof which is further combined with calcium and vitamins.

As a fraction containing collagen used in the present invention, skin protein fraction, bone protein fraction, lyophilization product of pulverized and skim corium layer, lyophilization product of pulverized and decalcified bone, and fraction which is produced by treating skin protein fraction or bone protein fraction with acid or alkaline can be exemplified. Further, a degradation product which is produced by hydrolysis with a proteolytic enzyme and has a molecular weight of 2–150 kDa can be used.

DETAILED DESCRIPTION OF THE INVENTION AND PREFERRED EMBODIMENTS

Figure 1:
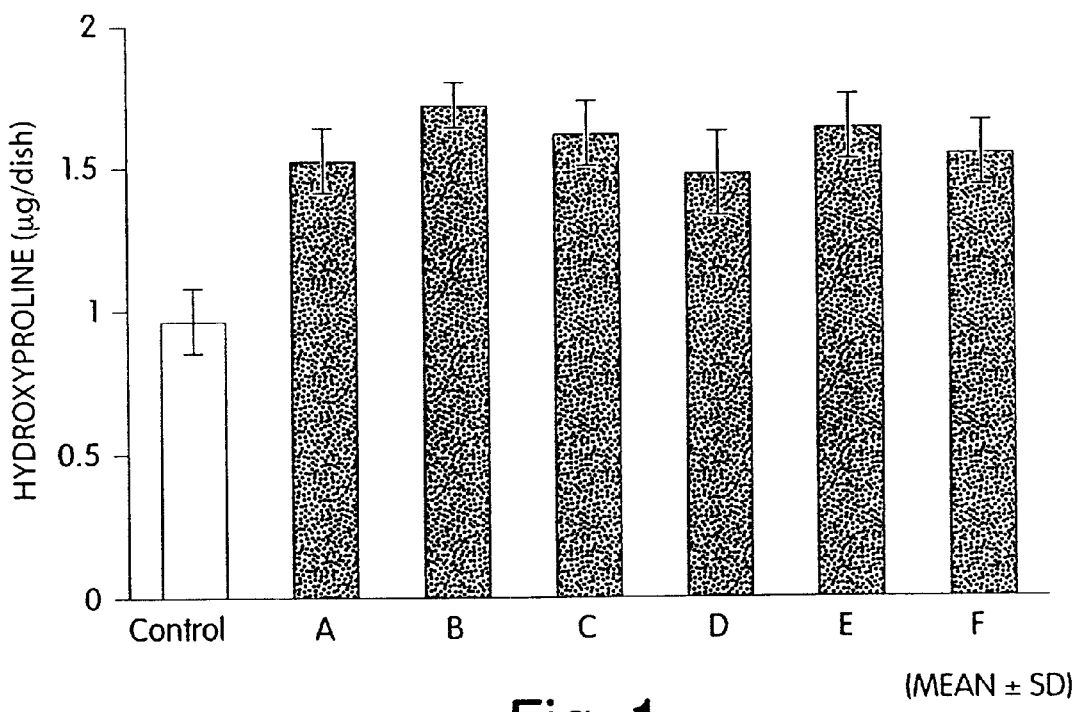
FIG. 1 represents an action of promoting collagen synthesis in osteoblast by a fraction containing collagen or degradation product thereof obtained in test example 2.

In the present invention, collagen, a fraction containing collagen and/or degradation product thereof can be combined with a medicine, drink, food or feed for having an action of strengthening bone. This fraction containing collagen is a protein fraction obtained from skin or bone. For example, when it is prepared from skin, skin can be depilated and corium layer was cut off. The tissue can be cut into pieces with a high-speed cutter, defatted with organic solvent and lyophilized to give a fraction containing collagen. When it is prepared from bone, bone can be decalcified with acid etc., pulverized with a high-speed cutter, decalcified, again, with acid etc., and lyophilized to give a fraction containing collagen. Collagen can be purified by treating skin protein fraction or bone protein fraction containing collagen with acid or alkaline. Treatment with acid or alkaline can be carried out by soaking these fractions in a liquid solution containing 5–30% of liquid solution of acid, such as hydrochloric acid or nitric acid, or alkaline, such as sodium hydroxide or potassium hydroxide, at 20–50° C. for 0.5–3 hours. After soaking, these fractions should be sufficiently washed with water. Hot water extraction of these fractions can be carried out by treating them with 70–80° C. hot water.

Further, these fractions containing collagen can be hydrolyzed by a proteolytic enzyme, such as pepsin, trypsin, chymotrypsin, etc., whose solubility can be enhanced and used. Hydrolysis by a proteolytic enzyme can be carried out by pulverizing fractions described before, suspending them in water, adding about 1% of proteolytic enzyme thereto and keeping it at 37° C. for 0.5–6 hours. After hydrolysis, the reaction mixture was heated to deactivate proteolytic enzyme and ultrafiltrated, followed by collection of filtrate. Hydrolysis can be preferably carried out so that the molecular weight of degradation product will be 2–200 kDa.

In addition, calcium or vitamins can be combined with these fractions containing collagen. As a calcium source, calcium chloride, calcium carbonate, calcium lactate, egg shell or milk-derived calcium can be used. As combination rate of calcium with fraction containing collagen, 0.5–5.0 weight parts of said fraction will be preferable to 1 weight part of calcium. As vitamins, any vitamin can be used however vitamin $D_3$ or a substance containing vitamin $D_3$ is preferably used. As raw material containing substantial amount of collagen, fresh skin or bone of cattle, pig, chicken, sheep and horse can be utilized.

In the present invention, collagen, fraction containing collagen and/or degradation product thereof can be combined with a medicine, such as tablet or powder, or with a drink or food, such as milk, yogurt, ice cream, milk drink, coffee drink, juice, jelly, noodle, cracker, bread or sausage, for endowing an action of strengthening bone. Further, in the same manner, these fractions or degradation product can be combined with a feed for endowing an action of strengthening bone. In addition, calcium agents with good absorptivity, such as calcium chloride, calcium carbonate, calcium lactate, egg shell or milk-derived calcium,etc., or vitamin D can be combined so that the action of strengthening bone thereof will be enhanced.

In the present invention, since oral administration of 10–2,500 mg of collagen, fraction containing collagen and/or degradation product thereof per day in an adult can exhibit an action of strengthening bone, collagen, fraction containing collagen, and/or degradation product thereof can be combined with a medicine drink or food by considering the above effective amount. Acute toxicity of fractions containing collagen, such as skin protein fraction or bone protein fraction was not observed in rat.

Since a medicine, drink, food or feed combined with collagen, fraction containing collagen and/or degradation product thereof has an action of strengthening bone, oral administration of these will be useful for prevention and/or treatment of bone metabolic diseases such as osteoporosis etc.

In addition, strengthening bone of livestock or poultry can be also carried out by combining collagen, fraction containing collagen and/or degradation product thereof with feed.

Preparation of fractions containing collagen and degradation products thereof, and an action of strengthening bone will be described by exemplifying reference examples and test examples as below. Further, the present invention will be illustrated by examples. However, these examples will not limit the scope of the present invention.

Reference Example 1

Porcine skin (10 kg) was depilated and corium layer was taken, minced into pieces with a high-speed cutter, defatted with a solvent of hexane:ethanol (5:1) and lyophilized to yield 1,354 g of skin protein fraction (fraction A) containing collagen. This fraction contained 85% of protein and the molecular weight distribution thereof was 50–200 kDa. The amount of protein was determined according to Lowry method (Lowry O.H., et al. (1951) J. Biol. Chem., 193, 265–275). Molecular weight distribution was determined by SDS polyacrylamide electrophoresis. The amount of protein and molecular weight distribution described below were also determined by the same method as the above.

Reference Example 2

The skin protein fraction (1,000 g) containing collagen obtained in reference example 1 was suspended in water so that its concentration would be 5%, followed by soaking it in an liquid solution of hydrochloric acid so that its concentration would be 10% and washed sufficiently with water. Then, it was again suspended in water so that its concentration would be 10% and heated at 90° C. for 30 min., followed by lyophilization to yield 620 g of skin protein fraction (fraction B) containing collagen. This fraction contained 93% of protein and the molecular weight distribution thereof was 50–200 kDa.

Reference Example 3

The skin protein fraction (300 g) containing collagen obtained in reference example 2 was suspended so that its concentration would be 5% and 1% pancreatin (Sigma) was added thereto, which was kept at 37° C. for 2 hours and, then, heated at 80° C. for 10 min. to deactivate pancreatin, followed by lyophilization to yield 280 g of degradation product of skin protein fraction (fraction C) containing collagen. This fraction contained 95% of protein and the molecular weight distribution was 2–50 kDa.

Reference Example 4

Bovine bone powder (10 kg) was suspended in water so that its concentration would be 10% and decalcified with treatment of hydrochloric acid so that its concentration would be 10%. Then, it was minced into pieces with a high-speed chopper and decalcified by soaking it in an liquid solution of hydrochloric acid so that its concentration would be 10%. Further, it was sufficiently washed with water, lyophilized and pulverized with a pulverizer to yield 2,210 g of bone protein fraction (fraction D). This fraction contained 89% of protein and the molecular weight distribution thereof was 50–150 kDa.

Reference Example 5

The bone protein fraction (1,000 g) containing collagen obtained in reference example 4 was suspended in water so that its concentration would be 5%, followed by soaking it in sodium hydroxide solution so that its concentration would be 10% and washed sufficiently with water to yield 540 g of bone protein fraction (fraction E) containing collagen. This fraction contained 92% of protein and the molecular weight distribution was 50–150 kDa.

Reference Example 6

The bone protein fraction (300 g) containing collagen obtained in reference example 5 was suspended so that its concentration would be 5% and 1% pancreatin (Sigma) was added thereto, which was kept at 37° C. for 2 hours and, then, heated at 80° C. for 10 min. to deactivate pancreatin, followed by lyophilization to yield 290 g of degradation product of bone protein fraction (fraction F) containing collagen. This fraction contained 95% of protein and the molecular weight distribution was 3–70 kDa.

Test Example 1

Fractions A-F obtained in reference examples were investigated with respect to an action of inhibiting bone resorption. Long bone were extirpated from 10–20 days old ICR mice and the whole bone marrow cells comprising osteoclast were obtained by depriving soft tissue from the bones and mincing the bones in α-modified minimum essential medium (α-MEM) containing 5% bovine fetal serum mechanically. About $2 \times 10^6$ of these cells in α-MEM containing 5% bovine fetal serum were placed on a piece of dentinum. Two hours after then, a test sample in α-MEM containing 5% bovine fetal serum was added so that the final concentration would be 10 μg/ml, which was cultured for 5 days and bone resorptive activity of osteoclast was investigated. Analysis of bone resorption was carried out by depriving cells from a piece of dentinum after cultivation thereof, staining them with Hematoxylin dye and counting the number of bone resorptive pit by morphometrical analysis with PIALA-555. As control, culture without any addition was used and bone resorptive activity of each case was calculated by defining 100% as that in the case of non-added group. The results were represented in table 1.

Comparing with bone resorptive activity of non-added group, any group with addition of fraction A-F which was skin protein fraction or bone protein fraction and contained collagen obtained in reference examples was found to have an action of inhibiting bone resorption.

TABLE 1

|  | Bone resorptive activity |
|---|---|
| Control | 100 (%) |
| Fraction A | 86 |
| Fraction B | 84 |
| Fraction C | 85 |
| Fraction D | 81 |
| Fraction E | 75 |
| Fraction F | 84 |

Test Example 2

Action of promoting collagen synthesis of fractions A-F obtained in reference examples was studied. That is, $2 \times 10^4$ cells/ml of osteoblastic cell line MC3T3-E1 in α-MEM containing 10% bovine fetal serum (Flow Laboratories) was inoculated in each well of 96-well plate and cultured at 37° C. for 24 hours in the presence of 5% $CO_2$. Then, the medium was changed into α-MEM, which did not contain bovine fetal serum, to which fractions A-F obtained in reference examples was added so that the final concentration thereof would be 10 μg/ml and cultured at 37° C. for 3 days. After then, the amount of synthesized collagen was measured by determining hydroxyproline. Determination of hydroxyproline was carried out by hydrolyzing suspension of punctured cultured cells with 6N hydrochloric acid and using p-dimethyl-aminobenzaldehyde according to Woessner's method (Woessner, J. F., Arch. Biochem. Biophys., vol.93, pp440–447, 1961) and the results were represented in FIG. 1. The amount of hydroxyproline in culture with addition of fractions A-F obtained in reference examples which were skin protein fraction or bone protein fraction and contained collagen was higher than that in culture without addition of those fractions, which suggested stimulation of collagen synthesis in osteoblast by the fractions.

Test Example 3

Action of strengthening bone of fraction B, C, E and F were studied in animal experiments. Osteoporotic model rats were made by ovarectomy of 6-weeks-old female SD rats after raising for 1 week and feeding with low calcium diet for 2 months and used in animal experiments. These rats were divided into 5 groups consisting of 7 rats, that is, control group, 1.5% fraction B administered group (I group), 1.5% fraction C administered group (II group), 1.5% fraction E administered group (III group) and 1.5% fraction F administered group (IV group) and fed with test diets consisting of components represented in table 2 for 1 month. In addition, 7 sham rats were also made by sham operation wherein ovary was not extirpated and used in the same experiments. As calcium source of mineral mixture in table 2, calcium carbonate was used.

TABLE 2

|  | Control g. | *Sham g. | *I group | II group | III group | IV group |
|---|---|---|---|---|---|---|
| Sucrose | 49.3 | 49.3 | 49.3 | 49.3 | 49.3 | 49.3 (g/100 g) |
| Casein | 20.0 | 20.0 | 18.5 | 18.5 | 18.5 | 18.5 |
| Corn starch | 15.0 | 15.0 | 15.0 | 15.0 | 15.0 | 15.0 |
| Cellulose | 5.0 | 5.0 | 5.0 | 5.0 | 5.0 | 5.0 |
| Corn oil | 5.0 | 5.0 | 5.0 | 5.0 | 5.0 | 5.0 |
| Vitamin mix.** (including choline) | 1.2 | 1.2 | 1.2 | 1.2 | 1.2 | 1.2 |
| Mineral mix.** | 4.5 | 4.5 | 4.5 | 4.5 | 4.5 | 4.5 |
| Fraction B |  | 1.5 |  |  |  |  |
| Fraction C |  |  | 1.5 |  |  |  |
| Fraction E |  |  |  |  | 1.5 |  |
| Fraction F |  |  |  |  |  | 1.5 |

*g.:group, **mix.:mixture

In addition, test diets consisting of components represented in table 3 were also fed in another experimental groups, that is, (1.5% fraction B+milk-derived calcium+vitamin $D_3$ 400 IU)administered group(V group), (1.5% fraction E+milk-derived calcium+vitamin $D_3$ 400 IU) administered group (VI group), 0.2% fraction B administered group, 2.0% fraction B administered group. As calcium source in mineral mixture, calcium carbonate was used in VII group and VIII group and milk-derived calcium (Japanese published unexamined patent application No. 6-125740) was used in V group and VI group. In test diets in table 2 and table 3, the amount of casein was adjusted so that nitrogen content in the all test diets would be the same. And in 100 g of test diet, 400 mg of calcium and 300 mg of phosphate were contained.

TABLE 3

|  | V group | VI group | VII group | VIII group |
|---|---|---|---|---|
| Sucrose | 49.3 | 49.3 | 49.3 | 49.3 (g/100 g) |
| Casein | 18.5 | 18.5 | 19.8 | 18.0 |
| Corn starch | 15.0 | 15.0 | 15.0 | 15.0 |
| Cellulose | 5.0 | 5.0 | 5.0 | 5.0 |
| Corn oil | 5.0 | 5.0 | 5.0 | 5.0 |
| Vitamin mix.* (including choline) | 1.2 | 1.2 | 1.2 | 1.2 |
| Mineral mix.* | 4.5 | 4.5 | 4.5 | 4.5 |
| Fraction B | 1.5 |  | 0.2 | 2.0 |
| Fraction E |  | 1.5 |  |  |

*mix.:mixture

Figure 2:
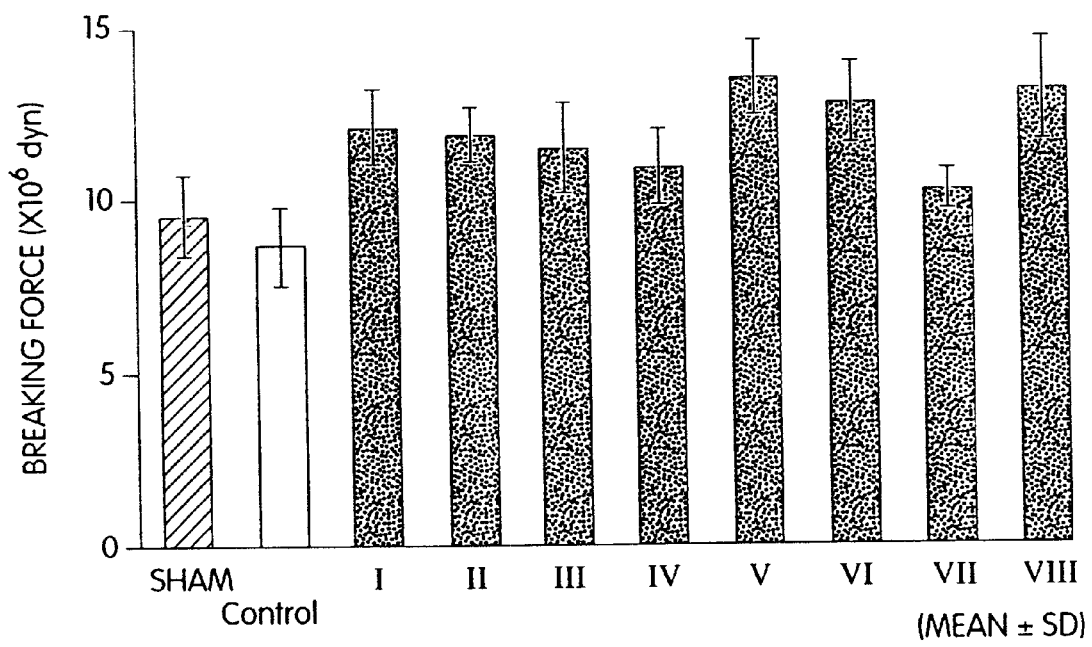
FIG. 2 represents breaking force of rat femur administered orally with fraction containing collagen or degradation product thereof obtained in test example 3.

After 1 month administration, femurs of rats in each test group were taken and breaking force thereof was determined by a breaking force analyzer (Rheometer, Max RX-1600, I-thechno), whose results were represented in FIG. 2.

As represented in this figure, fractions B, C, E and F which were skin protein fractions or bone protein fractions and comprised collagen were found to have significant action of strengthening bone. Action of bone strengthening thereof were found to be augmented by combination with milk-derived calcium having good absorptivity and vitamin $D_3$. Further, since there was significant difference with respect to bone strength when the ratio of calcium to collagen was 1.0:0.5–5.0, combination of 0.5–5.0 weight part of fraction containing collagen with 1 weight part of calcium was found to be effective.

The present invention will be explained by exemplifying examples.

Example 1

A tablet having action of strengthening bone was prepared by mixing raw materials represented in table 4 and formulating it under pressure.

TABLE 4

| | |
|---|---|
| Crystalline glucose hydrate | 73.5 (weight %) |
| Fraction F in reference example 6 | 20.0 |
| Calcium | 5.0 |
| Sugar ester | 1.0 |
| Flavor | 0.5 |

Example 2

A drink having action of strengthening bone was prepared by mixing raw materials represented in table 5, packing it in a container and sterilizing it by heating.

TABLE 5

| | |
|---|---|
| Mixed isomerized saccharide | 15.0 (weight %) |
| Fruit juice | 10.0 |
| Citric acid | 0.5 |
| Fraction A in reference example 1 | 0.5 |
| Flavor | 0.1 |
| Calcium | 0.1 |
| Water | 73.8 |

Example 3

A cracker having action of strengthening bone was prepared by mixing raw materials represented in table 6, making dough, formulating and baking it.

TABLE 6

| | |
|---|---|
| Wheat powder | 50.0 (weight %) |
| Sugar | 20.0 |
| Sodium chloride | 0.5 |
| Margarine | 12.5 |
| Egg | 12.1 |
| Water | 2.5 |
| Sodium bicarbonate | 0.1 |
| Ammonium bicarbonate | 0.2 |
| Calcium carbonate | 0.5 |
| Fraction B in reference example | 1.2 |

Example 4

A jelly having action of strengthening bone was prepared by mixing raw materials represented in table 7, packing it in container and sterilizing it by heating.

TABLE 7

| | |
|---|---|
| Fructose | 20.0 (weight %) |
| Granulated sugar | 15.0 |
| Miller jelly | 5.0 |
| Agar | 1.0 |
| Fraction A in reference example 1 | 0.5 |
| Flavor | 0.1 |
| Calcium | 0.1 |
| Water | 58.3 |

Example 5

A processed cheese having action of strengthening bone was prepared by mixing raw materials represented in table 8 and emulsifying it at 85° C.

TABLE 8

| | |
|---|---|
| Gouda cheese | 43.0 (weight %) |
| Cheddar cheese | 43.0 |
| Sodium citrate | 2.0 |
| Fraction B in reference example 2 | 0.5 |
| Milk-derived calcium | 1.0 |
| Water | 10.5 |

Example 6

After sterilizing 12 weight % reducing skim milk at 90° C. for 20 min., *Lactobacillus acidophilus* and *Streptococcus thermophilus* were inoculated to give 2 kinds of starter culture, which were mixed in the same amount. A yogurt having action of strengthening bone was prepared by mixing raw materials represented in table 9 and fermenting it.

TABLE 9

| | |
|---|---|
| Yogurt mix | 96.5 (weight %) |
| Starter culture | 3.0 |
| Fraction C in reference example 3 | 0.5 |

Example 7

A powder milk for infant having action of strengthening bone was prepared by mixing raw materials represented in table 10.

TABLE 10

| | |
|---|---|
| Skim milk | 75.5 (weight %) |
| Whey protein concentrate | 2.4 |
| Lactose | 13.5 |
| Mineral mix | 0.3 |
| Water soluble vitamin mix | 0.3 |
| Fat containing fat-soluble vitamin | 7.5 |
| Fraction F in reference example 6 | 0.5 |

Example 8

A feed for dog having action of strengthening bone was prepared by mixing raw materials represented in table 11.

TABLE 11

| | |
|---|---|
| Soy bean cake | 12.0 |
| Skim milk powder | 14.0 |
| Soy bean oil | 4.0 |
| Corn oil | 2.0 |
| Palm oil | 28.0 |
| Corn starch | 15.0 |
| Wheat powder | 8.0 |
| Wheat bran | 2.0 |
| Vitamin mix | 9.0 |
| Mineral mix | 2.0 |
| Cellulose | 3.0 |
| Fraction A in reference example 1 | 1.0 |

We claim:

1. A method of enhancing bone strength in a mammal comprising the steps of
    a) isolating collagen from animal skin or bone;
    b) degrading the collagen of step (a);
    c) combining the degraded collagen of step (b) with calcium and vitamin $D_3$;
    d) orally administering to a mammal in need of enhanced bone strength a composition comprising the combination of step (c) in an amount effective to strengthen bone.

2. The method of claim 1, degradation step (b) includes enzymatic degradation of collagen.

3. The method of claim 1, wherein the degradation step (b) includes limited acid or alkaline proteolysis of collagen.

4. The method of claim 1, wherein said amount of degraded collagen administered the subject is between 10 to 2500 mg.

5. The method of claim 1, said composition having a weight ratio of collagen to calcium of about 1.0 to 0.5–5.0.

6. The method of claim 1, said composition having a weight ratio of collagen to calcium of about 0.5–5.0.

7. The method of claim 1, wherein the calcium is selected from the group consisting of calcium chloride, calcium carbonate, calcium lactate, egg-shell derived calcium and milk derived calcium.

* * * * *

UNITED STATES PATENT AND TRADEMARK OFFICE
CERTIFICATE OF CORRECTION

PATENT NO. : 6,344,437 B1
DATED : February 5, 2002
INVENTOR(S) : Yukihiro Takada et al.

It is certified that error appears in the above-identified patent and that said Letters Patent is hereby corrected as shown below:

Column 9,
Lines 8 and 9, claim 5 should read:
5. The method of claim 1, said composition having a weight ratio of collagen to calcium of about 0.5-5.0.

Column 10,
Lines 1 and 2, claim 6 should read:
6. The method of claim 1, said composition having a weight ratio of collagen to calcium of about 3.75.

Signed and Sealed this

Nineteenth Day of August, 2003

JAMES E. ROGAN
*Director of the United States Patent and Trademark Office*